United States Patent [19]

Hawkins

[11] 3,993,702

[45] Nov. 23, 1976

[54] PRODUCTION OF UNSATURATED ALCOHOLS

[75] Inventor: Harold M. Hawkins, Bartlesville, Okla.

[73] Assignee: Phillips Petroleum Company, Bartlesville, Okla.

[22] Filed: Sept. 29, 1975

[21] Appl. No.: 617,755

[52] U.S. Cl. .................... 260/632 B; 260/488 H; 260/615 A
[51] Int. Cl.² ........................................ C07C 29/00
[58] Field of Search ............................ 260/632 B

[56] References Cited

UNITED STATES PATENTS

| 2,308,192 | 1/1943 | Mikeska et al. ............ 260/638 R |
| 2,335,027 | 11/1943 | Ritter ......................... 260/638 R |
| 2,848,500 | 8/1958 | Funck ........................... 260/606 |
| 2,943,701 | 7/1960 | Funck ........................... 260/606 |
| 3,414,588 | 12/1968 | Jones .......................... 260/638 R |
| 3,574,773 | 4/1971 | Mueller et al. ............. 260/638 R |
| 3,657,376 | 4/1972 | Stuebinger et al. ............ 260/681 |
| 3,696,155 | 10/1972 | Mueller et al. .............. 260/642 A |
| 3,962,848 | 9/1972 | Mueller et al. .............. 260/635 R |

FOREIGN PATENTS OR APPLICATIONS

| 980,028 | 1/1965 | United Kingdom ............ 260/606 |
| 1,005,439 | 9/1965 | United Kingdom ............ 260/606 |
| 1,071,767 | 6/1967 | United Kingdom ............ 260/606 |
| 1,110,802 | 4/1968 | United Kingdom ............ 260/606 |

OTHER PUBLICATIONS

Roberts, et al., "Basic Principles of Organic Chemistry", (1964), pp. 443–449.
Whitmore, "Organic Chemistry", 2nd ed. (1951), pp. 187, 188.
Arundale, et al., "Chem. Rev.", vol. 51 (1952), pp. 505–555.
Adkins, et al. "J. Amer. Chem. Soc.", vol. 2 (1928) pp. 499–503.

Primary Examiner—Joseph E. Evans

[57] ABSTRACT

A method for forming monoolefinic alcohols and optionally alkyl-substituted conjugated dienes. A lower alcohol is oxidized to the aldehyde, and the aldehyde separated from the product mixture by reaction with a monoolefinic alcohol to form a hemialdehyde. An aliphatic isomonoolefin is reacted with a portion of the hemialdehyde stream, to form additional unsaturated monoolefinic alcohol as product, and for recycle to the aldehyde recovery step. The unsaturated monoolefinic alcohol can be dehydrated to an alkyl-substituted conjugated diene such as isoprene.

15 Claims, 2 Drawing Figures though higher molecular weight species are suitable, though less preferred because of higher cost. Of these, most preferred is methanol since it is cheap and because the end product is the much preferred isoprene.

PRODUCTION OF UNSATURATED ALCOHOLS

FIELD OF THE INVENTION

The invention relates to a method to produce mono-olefinic alcohols. The invention also relates to a method to produce alkyl-substituted conjugated dienes.

BACKGROUND OF THE INVENTION

Monoolefinic alcohols have potential value in the production of alkyl-substituted conjugated dienes, such as isoprene. A convenient method of producing monoolefinic alcohols is to react an olefin such as isobutylene with an aldehyde. The aldehydes are readily produced by the oxidative treatment of a lower alcohol with a molecular oxygen-containing gas such as air.

However, a limiting factor in the feasibility of the process has been the difficulty in extracting the aldehyde from the reaction mixture resulting from the alcohol oxidation step. The oxidation step reaction product mixture contains unreacted alcohol, aldehyde, and water, and tends to form various close boiling admixtures or even azeotropic admixtures in some instances. Separation by conventional means, such as by fractional distillation, is difficult, expensive, or commercially impractical. Efforts to separate the aldehyde by treatment with an extraneous solvent have been helpful, but have necessitated the use of an additional and expensive material which always poses the likelihood of product contamination and interference in desired reactions since some of the extraneous solvent tends to recycle.

SUMMARY OF THE INVENTION

I have discovered an effective and useful scheme which recycles in part a monoolefinic alcohol product of the process to form a hemialdehyde with the aldehyde contained in the product mixture resulting from the alcohol oxidation step. The hemialdehyde can then be readily separated such as by fractional distillation means. The separated hemialdehyde is contacted with an aliphatic monoolefin, such as isobutylene, forming the desired monoolefinic alcohol. The monoolefinic alcohol is recovered in part, and in part recycled for formation and separation of additional hemialdehyde. The monoolefinic alcohol product can be utilized as an intermediate in the production of chemicals, or can be dehydrated to form alkyl-substituted butadienes, such as isoprene, for production of desirable rubbers and resins.

My process provides effective separation of aldehyde from the aldehyde production step by utilizing as the separating agent a product formed by my process and thus requires no extraneous solvent or added material. The process is simple, yet effective, and represents an economically practical approach to the production of monoolefinic alcohols and isoprene or substituted isoprenes.

DETAILED DESCRIPTION OF THE INVENTION

Figure 1:
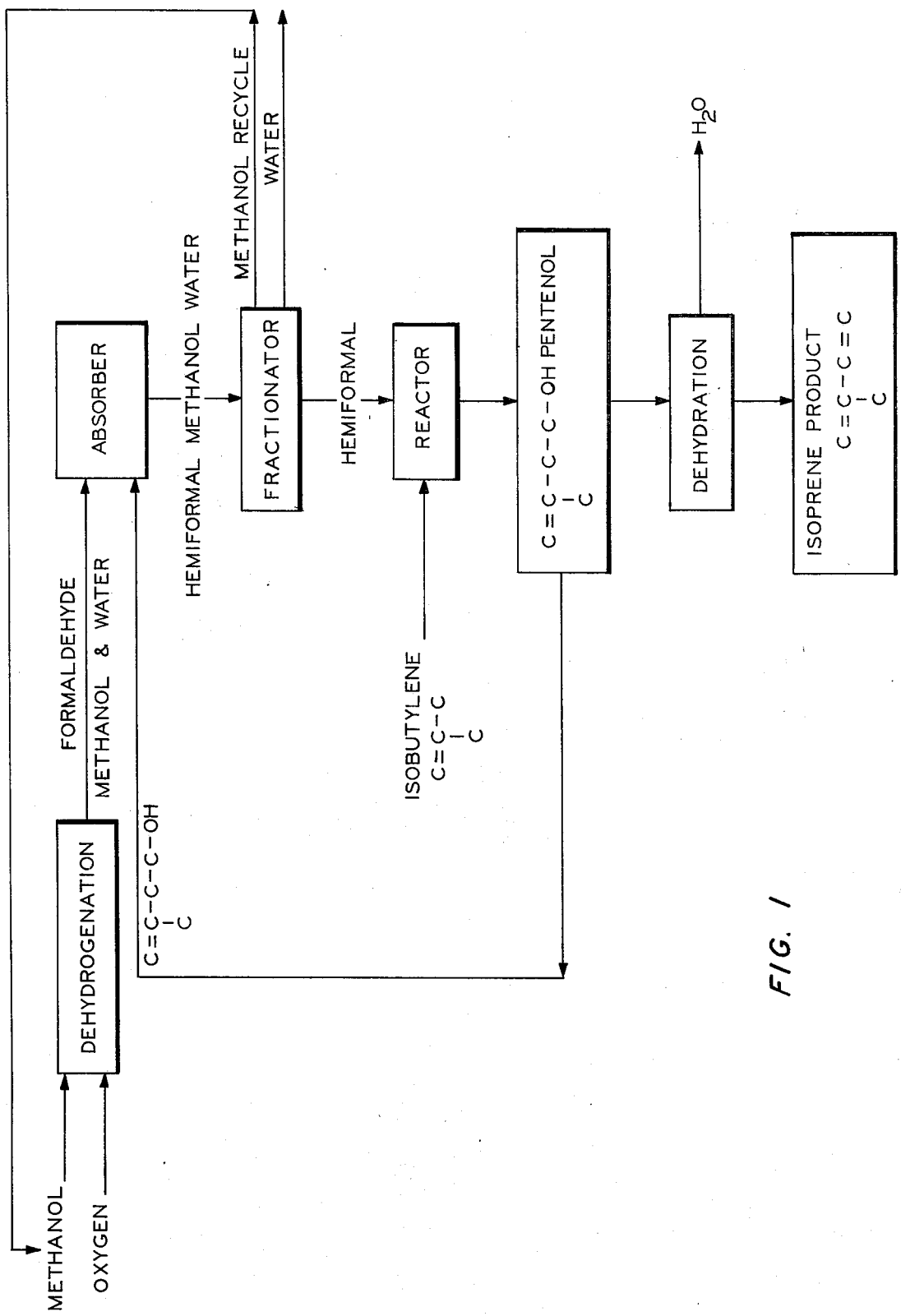
FIG. 1 illustrates by a block diagram the basic sequence of steps comprising the process. The simplest reactants are shown for exemplification purposes. Methanol and oxygen are dehydrogenated to form a reaction mixture of formaldehyde/methanol/water. This reaction mixture is contacted with recycle pentenol, 3-methyl-3-buten-1-ol, in an absorber, resulting in an admixture of hemiformal/methanol/water. The hemiformal admixture is fractionated, the methanol recovered and recycled, and the water disposed of as desired. The separated hemiformal is contacted with isobutylene to form 3-methyl-3-buten-1-ol. A portion of the 3-methyl-3-buten-1-ol is recycled back to the hemiformal formation step. A further portion is recovered, or, if desired, is dehydrated to form an isoprene product stream.

My invention provides a straightforward method for recovery of aldehyde after its formation from an alcohol/oxygen reaction step, utilizing for this important recovery step a product of the process step of reaction of an isobutylenic with the aldehyde. As before emphasized, my scheme is illustrated, in order to assist those skilled in the art by particular reference to methanol/formaldehyde/isobutylene/3-methyl-3-buten-1-ol/isoprene. However, my scheme is not limited solely to these basic reactants but is useful and effective for a reasonable range of reactants.

My process for the production of the monoolefinic alcohols and of alkyl-substituted butadienes such as isoprene comprises a series of reaction steps alternating with recovery steps, as illustrated in the attached block diagram.

An essential feature of my invention is that the unsaturated monoolefinic alcohol formed in the process is at least in part recycled back to the absorption step to react with the aldehyde to form additional hemialdehyde. Thus, the unsaturated monoolefinic alcohol formed by the process is employed as a reactant to form and recover a hemialdehyde, and can also be used to form by dehydration the alkyl-substituted conjugated diolefin. My process scheme requires no outside solvent or reactant to extract aldehyde formed in the oxidation of alcohol, but rather utilizes a product produced by the process itself.

Lower Alcohols

The first step in my process is a formation of the aldehyde from an alcohol. The alcohols employed are the lower hydrocarbyl aliphatic primary alcohols containing one alcohol group. These alcohols also can be represented by the general formula:

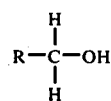

wherein R is hydrogen or a saturated hydrocarbyl aliphatic radical. Presently preferred are the lower alcohols wherein R contains 0 to 3 carbon atoms, though higher molecular weight species are suitable, though less preferred because of higher cost. Of these, most preferred is methanol since it is cheap and because the end product is the much preferred isoprene.

Exemplary monohydric alcohols include the presently preferred methanol, as well as ethanol, n-propanol, n-butanol, 2-methyl-propan-1-ol, n-pentanol, 1,2-dimethylpropan-1-ol, and the like. While mixtures can be employed, such are less desirable as resulting in a mixed end product which usually is less valuable.

Lower Aldehydes

The lower hydrocarbyl aliphatic monoaldehyde formed in the first step of my process scheme can be represented by:

wherein R is as defined hereinabove. Exemplary aldehydes are those corresponding to the exemplary alcohols above, such as formaldehyde, acetaldehyde, n-propanal, n-butanal, 2-methylpropanal-1, n-pentanaldehyde, 1,2-dimethylpropanal-1, and the like.

The aldehyde can be made by dehydrogenation by contacting an alcoholic vapor with a suitable catalyst and with a molecular oxygen-containing gas, such as air, in an amount insufficient for combustion. Any conditions known to the art can be employed. Exemplary conditions include contacting a mixture of air and a lower alcohol with a catalyst such as a silver gauze catalyst at a temperature of about 1100° F. to 1200° F., preferably for methanol about 1150° F., and at a pressure of about 3 psig to 10 psig, preferably for methanol about 4 psig. The lower alcohol feed stream is dehydrogenated at least in part to the corresponding aldehyde, and a portion of the resultant hydrogen reacts with oxygen to form water. Dehydrogenation generally is incomplete so that unreacted alcohol remains in the product stream from the oxidation step.

Alternative means for formation of the aldehyde include reaction of a lower alcohol with excess air over a molybdenum oxide catalyst at a temperature of about 450° F. to 550° F., and at a pressure of about 15 psia to 25 psia pressure.

Aliphatic Monoolefins

The aliphatic monoolefins are aliphatic hydrocarbyl isomonoolefins. These also can be termed methylene-substituted aliphatic hydrocarbons. These aliphatic hydrocarbyl isomonoolefin reactants contain the isobutylene group. These aliphatic monoolefins also can be represented by the general formula:

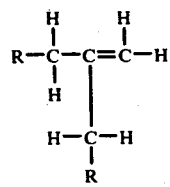

wherein each R is as defined above. Presently preferred are isomonoolefins wherein each R is hydrogen, such that the preferred species is isobutene or 2-methylpropene-1. Exemplary of the methylene-substituted aliphatic hydrocarbons are 2-ethylpropene-1, 2-n-propylpropene-1, 2-n-propylbutene-1, 2-isobutylhexene-1, 2-ethylbutene-1, 2-isopropylpentene-1, and the like. While mixtures can be employed, such are less desirable because of the resulting mixtures of products, usually less valuable, or which may require expensive resolution.

The reaction of a lower aldehyde with an isomonoolefin is an addition reaction resulting in the formation of aliphatic hydrocarbyl monoolefinic monoalcohols. The monoolefinics also can be represented by a generic formula:

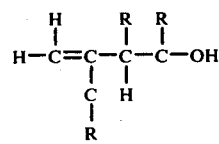

wherein each R is as defined above. These compounds contain a minimum of 5 carbon atoms per molecule. Of these, 3-methyl-3-buten-1-ol is preferred since it is most economically produced, and since it is a ready source of valuable isoprene.

In the formation of the hemialdehyde, the monoolefinic alcohol reacts with the lower aldehyde in a manner which can be illustrated in accordance with the following scheme, using formaldehyde and 3-methyl-3-buten-1-ol in skeletal form as typical reactants:

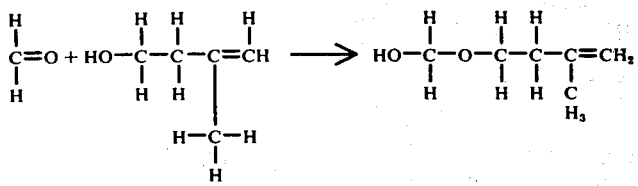

though the hemialdehydes are of variable composition. The hemialdehydes are typified by hemiformal which can be represented by $C_4H_9(CH_2O)_nOH$ wherein n ranges from about 1 to 3.

Figure 2:
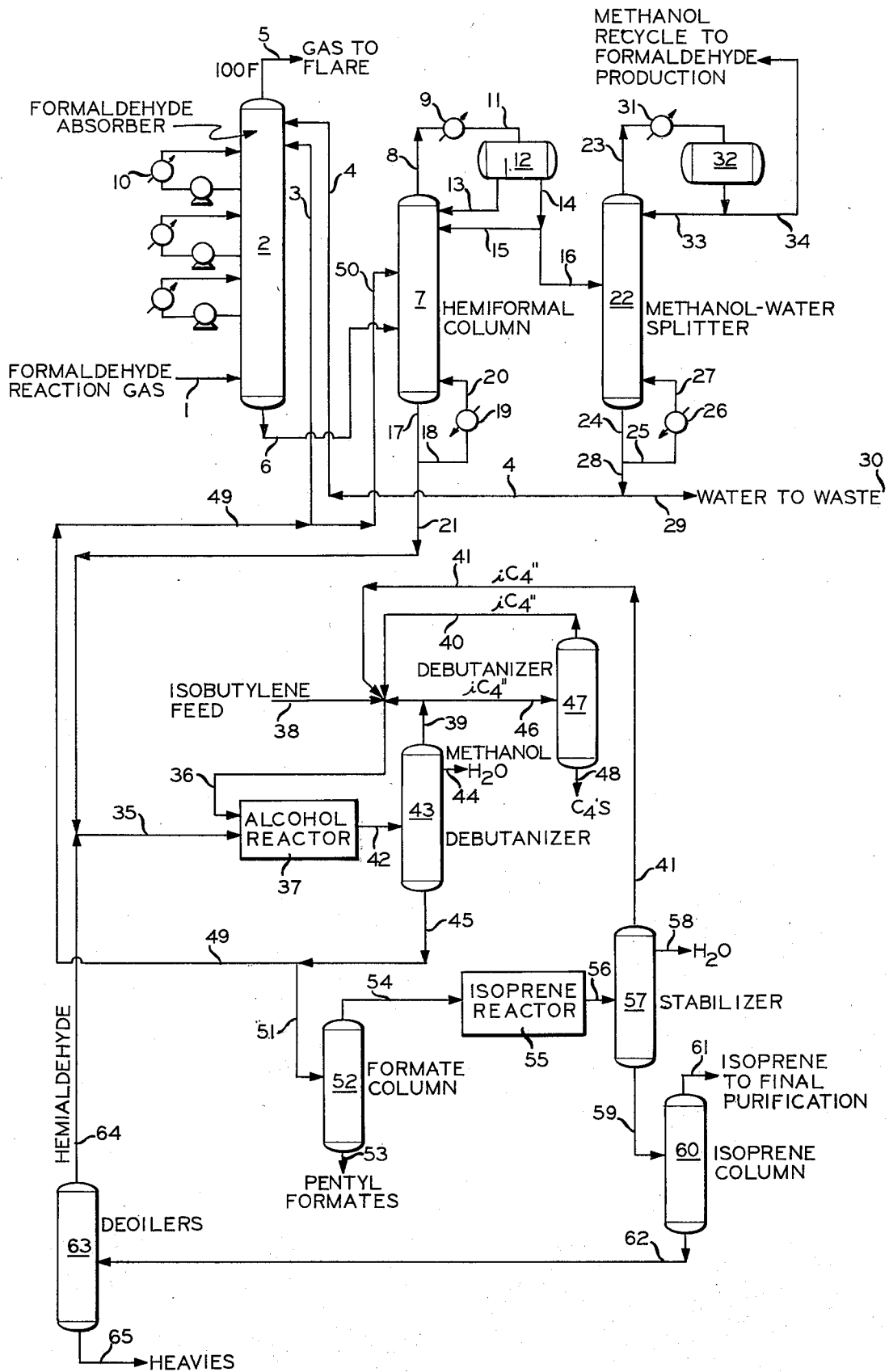
FIG. 2 represents a more detailed schematic diagram illustrating process equipment suitable to effectuate the scheme shown in FIG. 1. The sequence shown in FIG. 2 will be discussed in more detail hereinafter in conjunction with a material balance.

Referring to my FIG. 2, the description is illustrated by the preferred reactants for exemplary purposes, but the method is of general application to the reactants I have described.

Referring to my FIG. 2, formaldehyde reaction gases 1, from the formaldehyde reactor means (not shown), enter the formaldehyde absorber means 2 wherein they are contacted, preferably countercurrently, with a 3-methyl-3-buten-1-ol recycle stream 3. The absorption process can be conducted at a temperature in the range of about 100° to 150° F., preferably about 120° to 135° F., whereby the reaction of formaldehyde and 3-methyl-3-buten-1-ol forms a hemiformal. In the upper part of the absorber 2, recycle water 4 can be introduced to assist in the recovery of most of the remaining formaldehyde, methanol, and unreacted 3-methyl-3-buten-1-ol.

The temperature can be maintained in the desired range, since the reaction is exothermic, by suitable cooler means system 10, or, alternatively, by cooling coils (not shown) within the absorber means 2.

The fixed gases, saturated with water, are vented 5 from the top of the absorber column means 2, and can be flared as shown or otherwise sent to waste disposal. The pressure in absorber means 2 should be maintained slightly above atmospheric, such as about 2 psig to 20 psig, preferably 3 psig to 8 psig. The hemiformal solution 6 is withdrawn from the bottom of the absorber means 2. This stream 6 contains the absorbed formaldehyde, effectively as a hemiformal, together with methanol, and small amounts of formic acid from the formaldehyde production process.

By distillation of the hemiformal stream 6 in the hemiformal column means 7, light components 8 are separated from the absorber product 6. The distillation of fractionation column means 7 can be operated with a bottoms temperature of about 300° F. to 330° F., preferably about 320° F., or possibly somewhat less, so as to minimize decomposition of the hemiformal into formaldehyde and 3-methyl-3-buten-1-ol. The tendency for re-formation of lower aldehyde and unsaturated alcohol also can be minimized by introducing minor amounts of additional recycle 3-methyl-3-buten-1-ol, which nonobjectionably also can contain some formaldehyde as the hemiformal, as a side stream 15 into the hemiformal column means 7.

The hemiformal column means 7 overhead stream 8 comprises water, methanol, formic acid, and some unsaturated alcohol which in some cases, such as 3-methyl-3-buten-1-ol, may tend to azeotrope with the water. After condensing 9 at about 15 psia to 50 psia, preferably about 20 psia to 35 psia at approximately 100° F., the resultant overhead phase 11 is accumulated and separated 12 and returned in part 13 as reflux to the hemiformal column means 7 along with a portion 15 of the water phase 14 for suitable operation of the hemiformal column fractionator means 7.

The bottoms 17 from the hemiformal column means 7 comprises hemialdehyde, 3-methyl-3-buten-1-ol, pentyl formates, and water. A portion 18 is reboiled 20 in reboiler 19 for proper column operation, and the remainder 21 is employed as a hemiformal concentrate stream to the alcohol reactor means 37.

The remaining water phase product stream 16 from the hemiformal column 7 overhead 11 is fed to a methanol/water splitting means 22 and subjected to separation such as by fractionation means into a methanol recycle stream overhead 23 and a bottoms water stream 24. A portion 25 of the water stream 24 can be reboiled 26 and returned as reboil 27 to the formaldehyde absorber means 22 for efficient separation, and the remainder 28 can be removed 29 to waste disposal 30, or in part can be recycled 4 to the formaldehyde absorber means 2. The methanol overhead 23 is condensed 31 into an accumulator means 32 for recycle 33 as reflux to the formaldehyde absorber means 23 for efficient operation, and the remainder 34 can be otherwise utilized as desired, but for maximum economy in my process, the methanol stream 34 preferably is recycled to the initial methanol oxidation reaction step (not shown) to produce further formaldehyde reaction stream 1. If the waste water stream 30 contains any recoverable amounts of pentenols or other materials, it can be further treated as desired.

The bottoms product stream 21 of hemialdehyde from the hemialdehyde column means 7 can be combined with hemialdehyde 64 recovered from subsequent processing to create a hemialdehyde feed stream 35. The hemialdehyde stream 35 together with an isobutylene stream 36 are fed to an alcohol reactor means 37 for production of 3-methyl-3-buten-1-ol. Isobutylene feed 36 comprises fresh isobutylene feed 38 along with any recycle isobutylene such as all or part of 39, 40, and 41.

The reaction of formaldehyde and isobutylene results in:

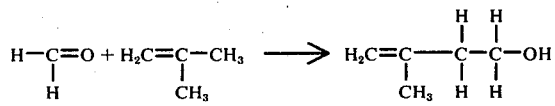

3-methyl-3-buten-1-ol, along with minor amounts of pentyl formate:

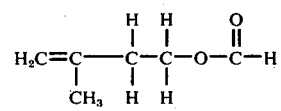

(3-methyl-3-buten-1-yl formate) plus some minor methanol formation also.

The reaction of isobutene and the lower aldehyde contained in or provided by the hemialdehyde takes place in reactor means 37, such as a continuous reactor, employing reaction conditions such as about 7 to 15, preferably 9 to 12, more preferably about 10, moles of isobutylene $iC_4''$ per mole formaldehyde in the feed; utilizing contacting temperature in the range of about 500° to 600° F., presently preferred about 520° to 560° F., more preferred such as about 545° F., under a pressure of about 1800 to 2500 psia, presently preferred about 1900 to 220, more preferred about 2000 psia; employing a suitable residence time such as about 25 to 40 minutes, presently preferred about 25 to 35, more preferred about 30 minutes. Under these conditions anticipated conversion of aldehyde is about 80 percent, with about 80 percent selectivity to 3-methyl-3-buten-1-ol.

Feed isobutylene stream 36 and hemialdehyde stream 35 can be heat exchanged with any of the reactor effluent streams such as 42 with suitable heat exchanger means (not shown) located between reactor vessels or by heat exchange surfaces within the vessels or walls.

Reactor effluent 42 is separated such as by fractionation in debutenizer means 43 into streams comprising recycle isobutylene 39, a methanol and water phase 44, and a bottoms product stream 45 containing 3-methyl-3-buten-1-ol, some unreacted aldehydes as the hemialdehyde, and some by-products such as the pentyl formates.

A portion 46 of recycle isobutylene 39 can be separated such as by fractionation in debutanizer means 47, if desired, to remove unreacted saturated $C_4$ components 48 to flare or other disposal, while the overhead 40 isobutylene and the rest of the recycle isobutylene 39 is returned to the isobutylene feed 36 to reactor means 37.

Bottoms product 45 from debutenizer means 43 can be split into a recycle stream 49 of 3-methyl-3-buten-1-ol used as extractant feed 3 for contact 2 with aldehyde stream 1, some recycle 50 of 3-methyl-3-buten-1-ol to the hemiformal column 7, and the remainder 51 3- methyl-3-buten-1-ol stream which contains the net production of 3-methyl-3-buten-1-ol, and by-product pentyl formates.

Separation 52, such as by fractionation, of 3-methyl-3-buten-1-ol stream 51 removes pentyl formates 53 at a fractionation temperature of about 260° F. to 300° F., preferably about 270° F. to 290° F., and a pressure of about 20 psia to 40 psia, preferably 20 psia to 25 psia, to produce a purified 3-methyl-3-buten-1-ol stream 54 for feed to a dehydration reactor means 55, or for other recovery as an olefinic alcohol product as may be preferred.

If an alkyl-substituted conjugated diene product is desired, the 3-methyl-3-buten-1-ol 54 can be dehydrated in reactor means 55 to form an isoprene product stream 56, using a temperature in the range of about 480° F. to 700° F., presently preferred about 550° F. to 600° F., more preferred about 570° F., under a pressure of about 15 psia to 100 psia, presently preferred about 20 psia to 40 psia, more preferred about 25 psia, employing an LHSV of 1 to 30, preferably about 2 to 5, more preferred about 3, employing a suitable dehydration catalyst such as pelleted tribasic calcium phosphate as described in U.S. Pat. No. 3,657,376.

Dehydration reactor means effluent 56 can be separated 57 such as by fractionation to remove isobutylene overhead 41 which can be returned to the alcohol reactor means 37, and water 58 which is removed. The bottoms product 59 contains isoprene, hemiformal, and heavies, and can be further separated such as by fractionation 60 to remove isoprene and any other $C_5$'s such as piperylene overhead 61 for such further purification, if any, as needed for particular rubber end products. The bottoms product 62 is mainly hemialdehyde which can be separated such as by fractionation means 63 into stream 64 for recycle 35 to the alcohol reactor 37, and a heavies reject 65 for disposal.

The alkyl-substituted butadienes produced in accordance with my process are those corresponding to dehydration products, such as isoprene, of the monoolefinic alcohols such as 3-methyl-3-buten-1-ol as described hereinabove.

The following is a typical anticipated material balance using the stream numbers as described hereinabove, and as correlated with my attached FIG. 2. The balance is not exact due to roundoff of the tabulated figures. Components listed as formaldehyde and pentenols may exist as hemialdehyde as described hereinabove.

MATERIAL BALANCE FORMALDEHYDE RECOVERY STEP QUANTITIES IN MOLES

| Stream No. | 1 | 3 | 4 | 5 | 6 | 16 | 21 | 28 | 29 | 34 | 50 |
|---|---|---|---|---|---|---|---|---|---|---|---|
| Hydrogen | 178 | | | 178 | | | | | | | |
| Oxygen | 4 | | | 4 | | | | | | | |
| Nitrogen | 1081 | | | 1081 | | | | | | | |
| CO+CO$_2$+CH$_4$ | 61 | | | 61 | | | | | | | |
| Water | 622 | | 613 | 203 | 1032 | 1000 | 32 | 995 | 382 | 5 | |
| Formaldehyde (CH$_2$O) | 582 | 37 | | 8 | 610 | 1 | 642 | | | 1 | 33 |
| Methanol | 165 | | | 15 | 150 | 150 | | | | 150 | |
| Formic Acid | 2 | | 3 | | 5 | 5 | | 5 | 2 | | |
| Pentenols | | 257 | | | 257 | | 486 | | | | 229 |
| Pentyl Formates | | 19 | | | 19 | | 35 | | | | 16 |
| Total | 2694 | 313 | 616 | 1550 | 2073 | 1156 | 1195 | 1000 | 384 | 156 | 278 |
| Stream No. | 35 | 36 | 38 | 39 | 41 | 42 | 46 | 48 | 58 | 59 | 64 |
| Water | 32 | | | | | 32 | | | 416 | | |
| Formaldehyde | 763 | | | | | 152 | | | | 121 | 121 |
| Methanol | | | | | | 41 | | | | | |
| Formic Acid | | | | | | | | | | | |
| Isobutylene | | 7600 | 499 | 7073 | 38 | 7073 | 707 | 10 | | | |
| N Butylenes | | 43 | 3 | 40 | | 40 | 4 | | | | |
| Isobutane | | 200 | 2 | 200 | | 200 | 20 | 2 | | | |
| Pentenols | 572 | | | | | 1061 | | | | 86 | 86 |
| Pentyl Formates | 35 | | | | | 76 | | | | | |
| Isoprene | | | | | | | | | | 414 | |
| Piperylene | | | | | | | | | | 2 | |
| Heavies (as C$_5$H$_{10}$O) | | | | | | | | | | 35 | |
| Total | 1402 | 7843 | 504 | 7313 | 38 | 8675 | 731 | 12 | 416 | 658 | 207 |
| Stream No. | 44 | 45 | 49 | 51 | 53 | 54 | 56 | 61 | 62 | 65 | |
| Water | 32 | | | | | | 416 | | | | |
| Formaldehyde | | 152 | 70 | 82 | | 82 | 121 | | 121 | | |
| Methanol | 41 | | | | | | | | | | |
| Formic Acid | | | | | | | | | | | |
| Isobutylenes | | | | | | | 38 | | | | |
| N Butylenes | | | | | | | | | | | |
| Isobutane | | | | | | | | | | | |
| Pentenols | | 1061 | 486 | 575 | | 575 | 86 | | 86 | | |
| Pentyl Formates | | 76 | 35 | 41 | 41 | | | | | | |
| Isoprene | | | | | | | | 414 | 414 | | |
| Piperylene | | | | | | | | 2 | 2 | | |
| Heavies (as C$_5$H$_{10}$O) | | | | | | | | 35 | 35 | 35 | |
| Total | 73 | 1289 | 591 | 698 | 41 | 657 | 1112 | 416 | 242 | 35 | |

The material balance illustrates an application of my process which utilizes a portion of a monoolefinic alcohol product stream as a reactant to recover aldehyde. In the material balance presented above, the unsaturated monoolefinic alcohol product further is converted to isoprene.

The disclosure, including data, illustrate the value and effectiveness of my invention. The examples, the knowledge and background of the field of the invention and general principles of chemistry and other applicable sciences, have formed the bases from which the broad descriptions of the invention including the ranges of conditions and generic groups of operant components have been developed, which have formed the bases for my claims here appended.

What is claimed is:

1. A method for forming alkenols which comprises the steps:
   a. oxidizing a lower alkanol at least in part to the corresponding lower alkanol,
   b. contacting said lower alkanol with an alkenol thereby forming a hemialdehyde,
   c. contacting said hemialdehyde with an alkene, thereby forming said alkenol,
   d. recycling a portion of said alkenol to said contacting step (b).

2. A method according to claim 1 wherein said oxidizing step (a) produces a product stream comprising said lower alkanol, together with water and unoxidized lower alkanol,
   wherein said (b) produces a hemialdehyde stream, said hemialdehyde product stream resulting from said contacting step (b) is separated into streams comprising a lower alkanol stream, a water stream, and a hemialdehyde concentrate, and said hemialdehyde concentrate is employed in said step (c),
   and wherein said lower alkanol stream is recycled to said oxidizing step (a).

3. A process according to claim 1 wherein said lower alkanol is a lower primary hydrocarbyl monoalcohol represented by the formula

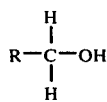

wherein R is hydrogen or a saturated hydrocarbyl aliphatic radical of up to 3 carbon atoms.

4. The process according to claim 3 wherein said lower alkanol is selected from the group consisting of methanol, ethanol, n-propanol, n-butanol, 2-methylpropan-1-ol, n-pentanol, 1,2-dimethylpropan-1-ol, and mixtures.

5. The process according to claim 1 wherein said alkanal is a lower hydrocarbyl aliphatic monoaldehyde represented by the formula

wherein R is hydrogen or saturated hydrocarbon aliphatic radical of up to 3 carbon atoms.

6. The process according to claim 5 wherein said alkanal is formaldehyde, acetaldehyde, n-propanal, n-butanal, 2-methylpropan-1-al, n-pentanaldehyde, 1,2-dimethylpropan-1-aldehyde.

7. The process according to claim 1 wherein said contacting of said alkene with said hemialdehyde produces an aliphatic hydrocarbyl monoolefinic alcohol represented by the formula:

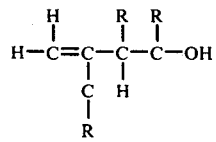

wherein each R is individually selected from hydrogen or a saturated hydrocarbon aliphatic radical of up to 3 carbon atoms.

8. The process according to claim 1 wherein said alkene is represented by:

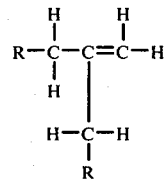

wherein each R is hydrogen or a saturated hydrocarbon aliphatic radical of up to 3 carbon atoms per R group.

9. The process according to claim 8 wherein said alkene is 2-ethylpropene-1, 2-n-propylpropene-1, 2-ethylbutene-1, 2-n-propylbutene-1, 2-isopropylpentene-1, or 2-isobutylhexene-1.

10. The process according to claim 1 wherein said oxidizing step (a) is conducted employing a silver gauze catalyst at a temperature in the range of about 1100° F. to 1200° F., employing a pressure of about 3 psig to 10 psig.

11. The process according to claim 1 wherein said oxidizing step (a) is conducted with excess air employing a molybdenum oxide catalyst and a contacting temperature of about 450° F. to 550° F. at a pressure of about 15 psia to 25 psia.

12. The process according to claim 1 wherein said contacting step (b) is conducted at a temperature in the range of about 100° to 150° F.

13. The process according to claim 1 wherein said contacting step (c) is conducted at a temperature in the range of about 500° to 600° F., under a pressure of about 1800 to 2500 psia, employing a contacting time of about 25 to 40 minutes, and employing a contacting ratio of about 7 to 15 moles of alkene per mole of alkanal.

14. A method for forming monoolefinic alcohols, which comprises:
   oxidizing a lower alkanol-air mixture to form a first stream comprising an alkanal, unoxidized alkanol, and water;
   contacting said first stream with a recycle stream of alkenol;
   recovering therefrom a second stream comprising a hemialdehyde, unoxidized alkanol, and water;
   separating said second stream into a third stream comprising water and lower alkanol, and a fourth stream comprising a hemialdehyde concentrate;
   reacting said fourth stream with an isobutylene stream, thereby producing said alkenol;
   and recycling a portion of said alkenol as said recycle for the formation of further said hemialdehyde.

15. A process according to claim 14, including the steps of condensing at least a portion of said third stream to form a resultant stream, separating the resultant stream into an alkanol phase and a water phase, and recycling said alkanol phase to said oxidizing step as a portion of said lower alkanol.

* * * * *

UNITED STATES PATENT AND TRADEMARK OFFICE
CERTIFICATE OF CORRECTION

PATENT NO. : 3,993,702
DATED : November 23, 1976
INVENTOR(S) : Harold M. Hawkins It is certified that error appears in the above-identified patent and that said Letters Patent are hereby corrected as shown below:

Column 4, following line 16, the formula should read --

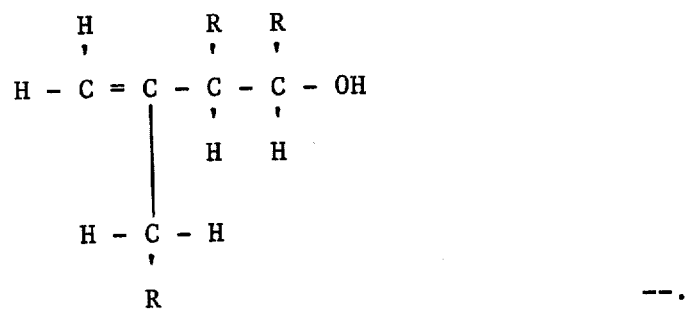

--.

Column 10, following line 12, the formula should read --

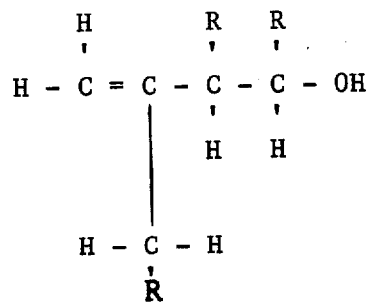

Signed and Sealed this sixteenth Day of August 1977

[SEAL]

Attest:

RUTH C. MASON
*Attesting Officer*

C. MARSHALL DANN
*Commissioner of Patents and Trademarks*